United States Patent [19]

Carlsson et al.

[11] Patent Number: 4,629,448
[45] Date of Patent: Dec. 16, 1986

[54] HOSE SET FOR EXTRACORPOREAL TREATMENT OF BLOOD AND SIMILAR LIQUIDS

[75] Inventors: Per-Oloy A. V. Carlsson, Sosdala; Rolf E. Karlberg, Verberod; Thore Falkvall, Helsingborg, all of Sweden

[73] Assignee: Gambro Lundia AB, Sweden

[21] Appl. No.: 530,081

[22] Filed: Sep. 7, 1983

[30] Foreign Application Priority Data

Sep. 10, 1982 [SE] Sweden ................ 8205159

[51] Int. Cl.⁴ ........................................ A61M 37/00
[52] U.S. Cl. ........................................ 604/4; 604/86; 604/153; 604/283
[58] Field of Search ................ 604/4–6, 604/86, 283, 153, 280; 128/DIG. 13; 417/474–477

[56] References Cited

U.S. PATENT DOCUMENTS

| | | | |
|---|---|---|---|
| 3,550,619 | 12/1970 | Halasz | 137/595 |
| 3,927,955 | 12/1975 | Spinosh et al. | 417/477 |
| 3,942,528 | 3/1976 | Loeser | 604/86 |
| 3,964,479 | 6/1976 | Boag et al. | 604/5 |
| 4,079,007 | 3/1978 | Hutchisson | 210/85 |
| 4,121,585 | 10/1978 | Becker, Jr. | 604/86 |
| 4,252,115 | 2/1981 | Schael | 604/29 |
| 4,253,456 | 3/1981 | Schindler et al. | 128/DIG. 13 |
| 4,300,551 | 11/1981 | Kinney | 604/5 |
| 4,411,786 | 10/1983 | Russell | 604/5 |
| 4,481,827 | 11/1984 | Bilstad et al. | 604/6 |
| 4,515,535 | 5/1985 | D'Silva | 604/153 |
| 4,526,515 | 7/1985 | De Vries | 417/477 |

FOREIGN PATENT DOCUMENTS

| | | |
|---|---|---|
| 0033080 | 1/1981 | European Pat. Off. . |
| WO81/02979 | 10/1981 | PCT Int'l Appl. ............ 604/4 |
| 2004092 | 3/1979 | United Kingdom ............ 604/5 |
| 2021418 | 12/1979 | United Kingdom . |

*Primary Examiner*—C. Fred Rosenbaum
*Assistant Examiner*—Michelle N. Lester
*Attorney, Agent, or Firm*—Lerner, David, Littenberg, Krumholz & Mentlik

[57] ABSTRACT

A tube set intended for extracorporeal treatment of blood and similar perishable liquids, e.g. by dialysis, includes a spacer adapted to rigidly connect an inlet end of a pump segment for a tube pump to an outlet end of the pump segment. The spacer is adapted to transfer liquid to and from the pump segment. Ports may be provided in the spacer for the purpose of withdrawing liquid samples from the spacer or supplying reagents or priming fluids to the liquid flowing through the spacer. A stay formed integrally with the spacer supports the spacer against the tube pump.

10 Claims, 5 Drawing Figures

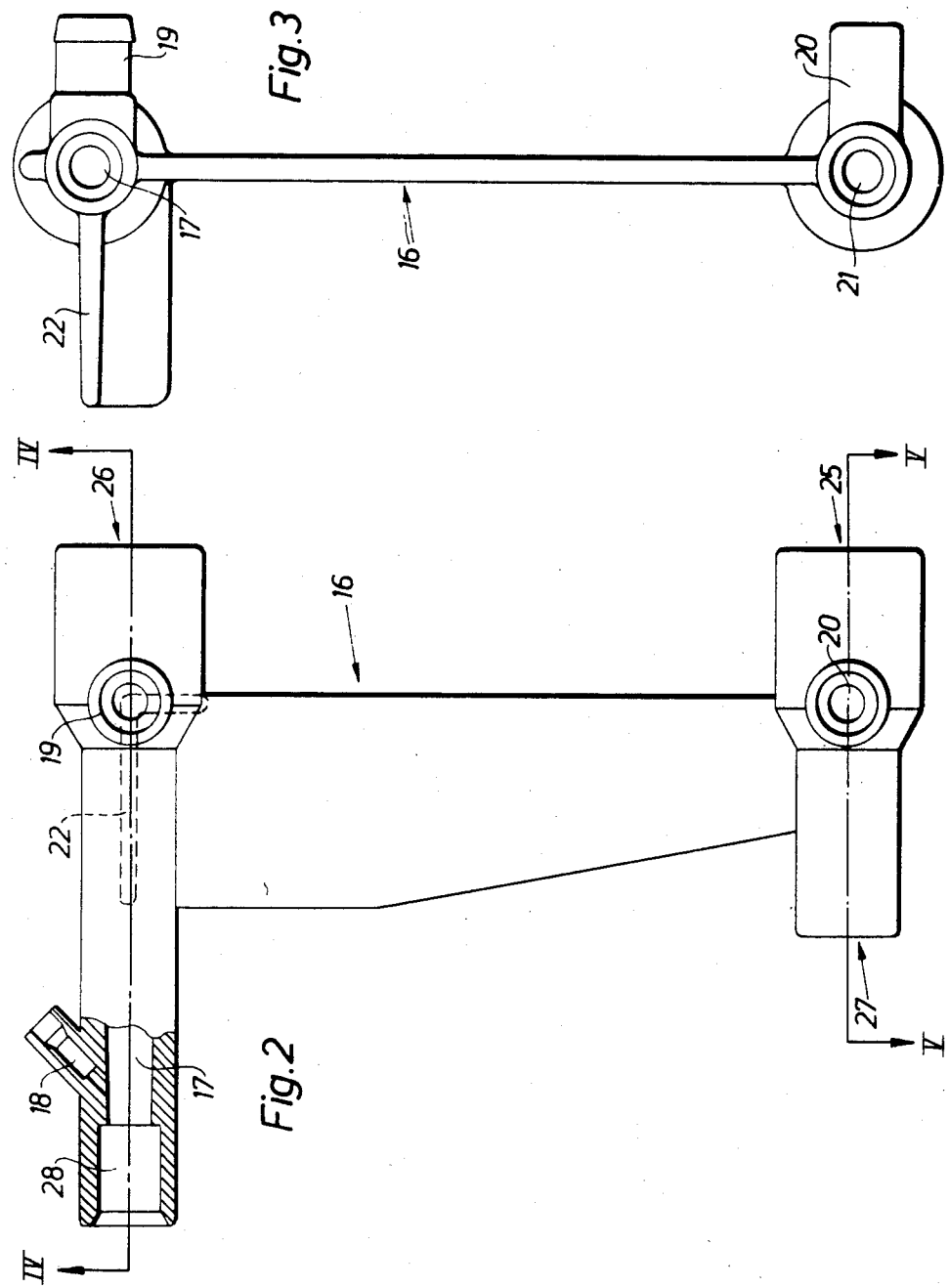

HOSE SET FOR EXTRACORPOREAL TREATMENT OF BLOOD AND SIMILAR LIQUIDS

FIELD OF THE INVENTION

The present invention relates to a tube set intended for extracorporeal treatment of blood and similar perishable liquids, e.g. by dialysis, comprising at least one pump segment adapted so as to be introduced into a tube pump or the like and provided with an inlet end and an outlet end.

Such tube sets normally are made to be used only once. They are frequently divided into an arterial branch and a venous branch, the arterial branch being intended to be coupled between one of the patient's arteries and the apparatus by means of which the blood is to be treated. The venous branch is intended instead to be coupled between the blood-treating apparatus and one of the patient's veins for the return of the blood. The expression "tube set" as used herein refers first and foremost to the arterial branch. However, the invention may also be applied to the venous branch or to a tube set consisting of combinations of the arterial branch and the venous branch.

BACKGROUND OF THE INVENTION

Present tube sets normally consist of a plurality of tubes which are joined to one another by numerous branch pipes, T-pipes or other components, such as pump segments, drip chambers, pressure monitoring pads or the like, by means of which the flowing medium can be controlled and/or guided. In addition, the tube set normally includes different types of ports for the feed and/or withdrawal of liquids, e.g. for dilution and/or sampling. The various components are usually distributed at different points along the tube set.

An object of the present invention is to facilitate the assembly of the tube set on the front of a control unit, the above-mentioned components and functions associated therewith being concentrated in one or a small number of points on the front of the control unit. If possible, therefore, the tube set should consist of an unbroken tube between the front of the control unit and the patient. In this manner, the personnel performing the treatment can concentrate on the control unit and on the patient.

It is another object of the invention to facilitate sampling and other treatment of the patient.

SUMMARY OF THE INVENTION

The present invention relates to a tube set intended for extracorporeal treatment of blood and similar perishable liquids, e.g. by dialysis, comprising at least one pump segment adapted so as to be introduced into a tube pump or the like and provided with an inlet end and an outlet end. The invention is characterized in that the inlet and outlet ends of the tube pump are rigidly connected to each other by a spacer, which facilitates assembly of the tube set, especially the pump segment, while also inhibiting the improper assembly of same.

The spacer preferably comprises four tube seats, two of which are adapted to receive the pump segment. The remaining two seats are adapted to receive an inlet portion and an outlet portion respectively of the tube set. Thus, the spacer facilitates the assembly of the tube set itself.

In a preferred embodiment of the invention, the inlet portion (i.e., the portion adapted for connection to an artery of a patient) comprises an arterial pressure monitor which is directly connected to the spacer. Normally, such an arterial pressure monitor consists of a plastic pad or the like whose internal pressure can be measured either from the outside or through any suitable connecting nozzle. By connecting the arterial pressure monitor directly to the spacer, a more compact construction is obtained, while also reducing the number of coupling points.

The spacer may also comprise one or more ports or the like for the supply and/or withdrawal of material, e.g. for dilution and/or sampling. Such ports or the like are normally arranged in branch pipes or T-pieces, and these can be omitted, therefore, if the ports are provided directly in the spacer.

The spacer preferably comprises a fitting adapted to connect the outlet end of the pump segment to the outlet portion of the tube set. The fitting is preferably adapted so as to comprise an inlet for the input of a reagent, e.g. heparin, and a port for sampling arranged upstream of the inlet. The distance between the inlet and the outlet end of the pump segment and the distance between the port and the outlet end of the pump segment are appropriately chosen so that sampling can take place without any risk of interference caused by the reagent introduced through the inlet being sucked back as a result of the suction generated in the pump segment.

In another embodiment of the invention, the spacer comprises a stay intended to support the spacer against the pump or any part firmly attached thereto during the assembly of the pump segment in the pump or during sampling. This facilitates not only assembly, but also any sampling through ports provided in the spacer.

The spacer may also include another fitting adapted to connect the inlet portion of the tube set to the inlet end of the pump segment. This fitting may include a port for the input of liquid, e.g. a priming liquid, with the aid of the pump.

BRIEF DESCRIPTION OF THE DRAWINGS

For a better understanding of the present invention, reference is made to the following detailed description of an exemplary embodiment considered in conjunction with the accompanying drawings, in which:

FIG. 2 is a top view of a spacer which forms part of the tube set shown in FIG. 1, a portion of the spacer being broken away to facilitate consideration and discussion;

FIG. 3 is a front view of the spacer shown in FIG. 2;

DESCRIPTION OF THE EXEMPLARY EMBODIMENT

Figure 1:
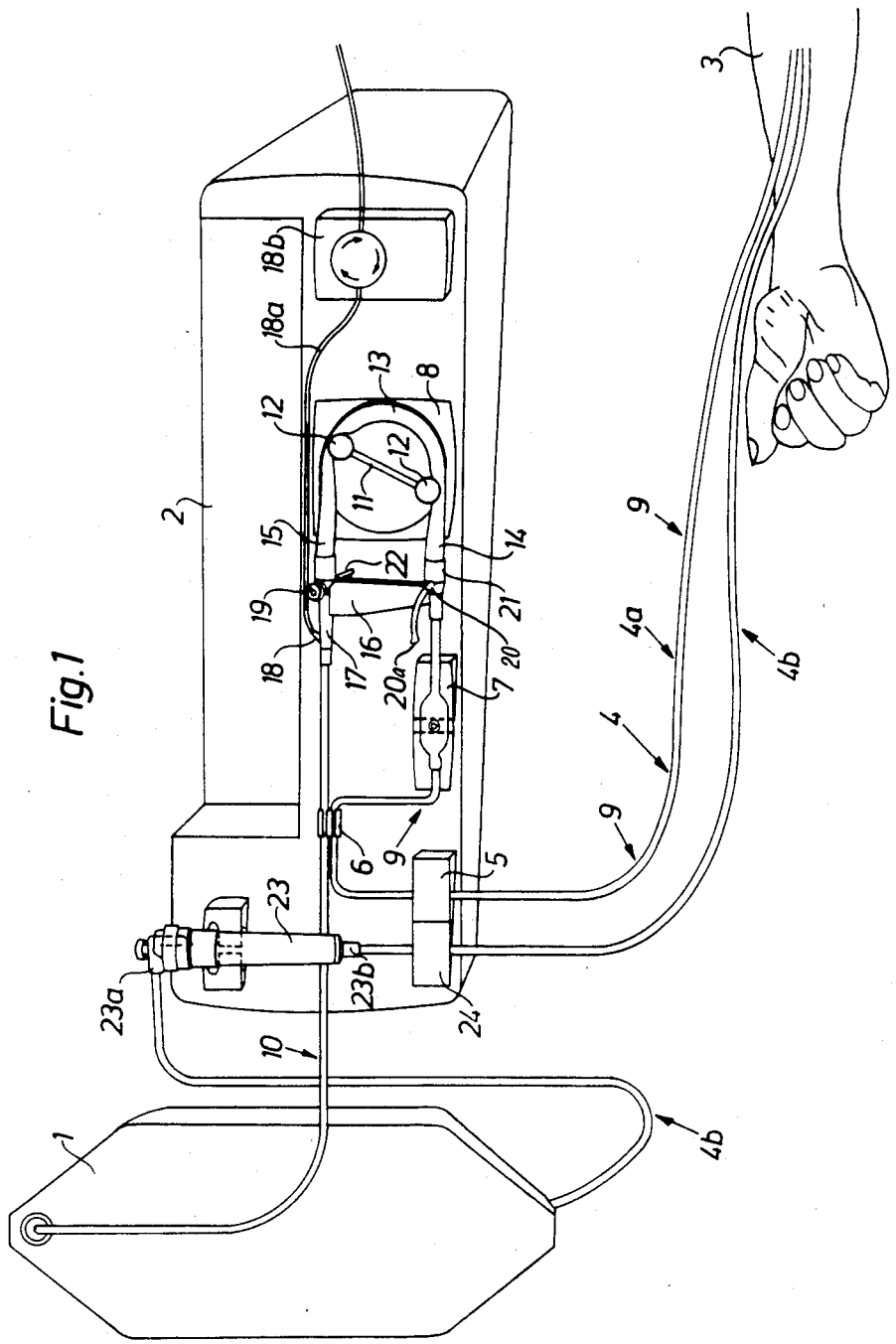
FIG. 1 is a schematic illustration of a dialyser connected to a control unit and a patient by a tube set consisting of an arterial branch and a venous branch.
Figure 4:
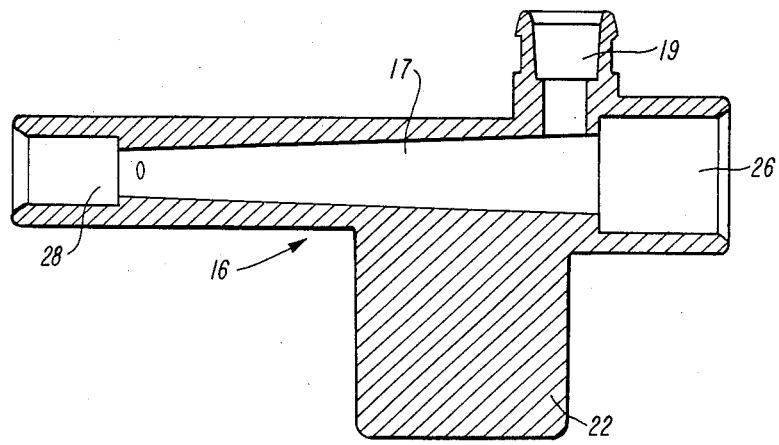
FIG. 4 is a cross-sectional view, taken along line IV—IV of FIG. 2 and looking in the direction of the arrows, of the spacer shown in FIG. 2.
Figure 5:
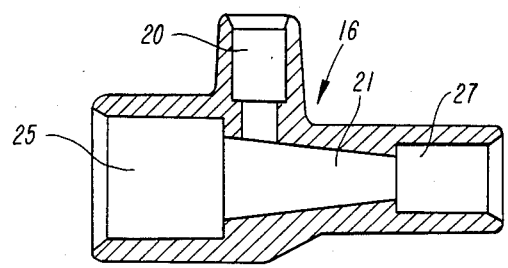
FIG. 5 is a cross-sectional view, taken along line V—V of FIG. 2 and looking in the direction of the arrows, of the spacer shown in FIG. 2.

Referring to FIG. 1, a dialyser 1, a control unit 2 and a patient 3 are coupled together by means of a tube set designated as a whole by reference numeral 4. This tube set consists of an arterial branch 4a and a venous branch 4b. The arterial branch 4a is connected by means of an injection needle (not shown) to one of the arteries of the patient 3 and passes through a shut-off clip 5, a holder 6 and an arterial pressure monitor 7 to a pump 8 and then to the dialyser 1. The portion of the arterial branch 4a extending from the patient 3 to the suction side of the pump 8 constitutes the inlet portion of the arterial branch 4a and is designated as a whole by reference numeral 9. The portion of the arterial branch 4a between the delivery side of the pump 8 and the dialyser 1 constitutes the outlet portion of the arterial branch 4a and is designated as a whole by reference numeral 10.

The invention resides primarily in the tube set 4. Accordingly, the control unit 2 has been shown only schematically without the instruments and many other components which are normally included therein.

The pump 8 comprises, in addition to a rotor 11 with two rollers 12 securely attached to the control unit 2, a pump segment 13 incorporated in the tube set 4. The pump segment 13 has an inlet end 14 and an outlet end 15 which are rigidly connected to each other by a spacer 16.

The spacer 16 includes between the outlet end 15 of the pump segment 13 and the outlet portion 10 of the arterial branch 4a a pipe fitting 17 adapted to connect the outlet end 15 of the pump segment 13 to the outlet portion 10 of the arterial branch 4a. The fitting 17, in turn, includes an inlet 18 for the input of a reagent, e.g. heparin, and a sampling port 19 arranged upstream of the inlet 18. The distance between the inlet 18 and the outlet end 15 of the pump segment 13 and the distance between the port 19 and the outlet end 15 of the pump segment 13 are chosen so that sampling through the port 19 can take place without any risk of interference caused by the reagent introduced through the inlet 18 being sucked back towards the port 19 as a result of the suction generated in the pump segment 13. A source of heparin or the like (not shown) is connected to the inlet 18 by a tube 18a and a pump 18b. The spacer 16 is also provided between the inlet portion 9 of the arterial branch 4a and the inlet end 14 of the pump segment 13 with a pipe fitting 21. The fitting 21 includes a port 20 for the input of a liquid, e.g. priming liquid, through a tube 20a with the help of the pump 8. Finally, the spacer 16 comprises a stay 22 designed to support the spacer 16 against the front of the control unit 2 or against any other component firmly attached to the pump 8 or to the control unit 2.

From the dialyser 1, venous branch 4b of the tube set 4 passes through a drip chamber 23, which has an inlet 23a and an outlet 23b, and a shut-off clip 24 back to the patient 3. The drip chamber 23 is described in greater detail in U.S. patent application Ser. No. 530,110, filed concurrently herewith and corresponding to Swedish patent application Ser. No. 8205160-8, which applications are incorporated herein by reference.

Referring now to FIGS. 2-5, where the spacer 16 is shown in greater detail, the fittings 21, 17 include seats 25, 26, respectively, for the inlet end 14 and the outlet end 15, respectively, of the pump segment 13. The fittings 21, 17 are also provided with seats 27, 28, respectively. The seat 27 is adapted to be coupled directly to the outlet end of the arterial pressure monitor 7 to thereby terminate the inlet portion 9 of the arterial branch 4a of the tube set 4. The seat 28 is adapted to be coupled directly to the outlet portion 10 of the arterial branch 4a of the tube set 4.

It will be understood that the embodiment described above is only exemplary and that a person skilled in the art may make many variations and modifications without departing from the spirit and scope of the present invention. For instance, the different ports mentioned above may be arranged so as to fulfill functions other than those mentioned by way of example. Furthermore, the tube set can be provided, of course, with additional components so as to perform other functions. Such additional components, such as the venous branch of the tube set with its drip chamber, are described in greater detail in U.S. patent application Ser. No. 530,110, filed concurrently herewith and corresponding to Swedish patent application No. 8205160-8, which applications have been incorporated herein by reference. All such modifications and variations are intended to be included within the scope of the invention as defined in the appended claims.

We claim:

1. A tube set adapted for use with a fluid treatment apparatus, said tube set including an inlet portion, an outlet portion, and a pump segment adapted for use with a tube pump mounted on a control unit of the fluid treatment apparatus, said pump segment including an inlet end for receiving fluid from said inlet portion of said tube set and an outlet end for delivering fluid into said outlet portion of said tube set, said tube set further including a spacer member adapted to rigidly position said inlet end and said outlet end of said pump segment a predetermined distance apart and to facilitate fluid connection of said inlet end and said outlet end of said pump segment to said inlet portion and said outlet portion of said tube set, respectively, said spacer member including a first end corresponding with said inlet end of said pump segment, a second end corresponding with said outlet end of said pump segment, and a bridging portion connecting said first and second ends of said spacer member, said bridging portion being substantially planar and being sized and shaped so as to facilitate movement of said spacer member relative to said control unit, said first end of said spacer member including a first tubular conduit including first and second coupling means for coupling said first tubular conduit to said inlet end of said pump segment and said inlet portion of said tube set, respectively, and said second end of said spacer member including a second tubular conduit including third and fourth coupling members for coupling said second tubular conduit to said outlet end of said pump segment and said outlet portion of said tube set, respectively, whereby said fluid can flow through said first tubular conduit between said inlet end of said pump segment and said inlet portion of said tube set and through said second tubular conduit between said outlet end of said pump segment and said outlet portion of said tube set.

2. A tube set according to claim 1, wherein each of said first, second, third and fourth Coupling Members includes a tube seat.

3. A tube set according to claim 1, further comprising an arterial pressure monitor positioned in said inlet portion of said tube set and directly connected to said second coupling means of said first tubular conduit.

4. A tube set according to claim 1, wherein said second tubular conduit includes supplying means for supplying a reagent to said liquid flowing through said second tubular conduit from said outlet end of said pump segment to said outlet portion of said tube set and withdrawing means arranged upstream from said supplying means for withdrawing a sample of the liquid flowing through said second tubular conduit, the distance between said supplying means and the outlet end of the pump segment and the distance between said withdrawing means and the outlet end of the pump segment being selected such that samples withdrawn from said withdrawing means are not interfered with by a reagent introduced through said supplying means being sucked back towards said withdrawing means as a result of suction generated in the pump segment of the tube pump.

5. A tube set according to claim 1, wherein said first tubular conduit includes supplying means for supplying additional liquid to the liquid flowing through said first tubular conduit from said inlet portion of said tube set to said inlet end of said pump segment.

6. A tube set according to claim 5, wherein said additional liquid is a priming liquid.

7. A spacer adapted to maintain a pump segment in a rigid position, said pump segment being adapted for use with a tube pump mounted on a control unit of a fluid treatment apparatus and including an inlet end and an outlet end, said spacer being adapted to maintain said inlet end and said outlet end of said pump segment a predetermined distance apart from each other and to facilitate fluid connection of said inlet end and said outlet end of said pump segment to a tube set including an inlet portion and an outlet portion, whereby said spacer facilitates fluid connection of said inlet portion of said tube set to said inlet end of said pump segment and of said outlet end of said tube set to said outlet end of said pump segment, said spacer comprising a first end corresponding with said inlet end of said pump segment, a second end corresponding with said outlet end of said pump segment, and a bridging portion connecting said first and second ends of said spacer member, said bridging portion being substantially planar and being sized and shaped so as to facilitate movement of said spacer member relative to said control unit, said first end of said spacer member including a first tubular conduit including first and second coupling means for coupling said first tubular conduit to said inlet end of said pump segment and said inlet portion of said tube set, respectively, and said second end of said spacer member including a second tubular conduit including third and fourth coupling members for coupling said second tubular conduit to said outlet end of said pump segment and said outlet portion of said tube set, respectively, whereby said fluid can flow through said first tubular conduit between said inlet end of said pump segment and said inlet portion of said tube set and through said second tubular conduit between said outlet end of said pump segment and said outlet portion of said tube set.

8. A spacer according to claim 7 wherein said second tubular conduit includes supplying means for supplying a reagent to the liquid flowing through said second tubular conduit from said outlet end of said pump segment to said outlet portion of said tube set and withdrawing means arranged upstream from said supplying means for withdrawing a sample of the liquid flowing through said second tubular conduit, the distance between said supplying means and the outlet end of the pump segment and the distance between said withdrawing means and the outlet end of the pump segment being selected such that samples withdrawn from said spacer through said withdrawing means are not interfered with by a reagent introduced through said supplying means being sucked back towards said withdrawing means as a result of suction generated in the pump segment of the tube pump.

9. A spacer according to claim 8 wherein said first tubular conduit includes injecting means for injecting additional liquid to the liquid flowing through said first tubular conduit from said inlet portion of said tube set to said inlet end of said pump segment.

10. A spacer according to claim 7, further comprising supporting means including a stay for supporting said spacer against said control unit.

* * * * *